US006524261B2

(12) United States Patent
Talish et al.

(10) Patent No.: US 6,524,261 B2
(45) Date of Patent: **\*Feb. 25, 2003**

(54) ULTRASOUND APPLICATION DEVICE FOR ACCELERATING STERNUM HEALING

(75) Inventors: Roger J. Talish, Hillsborough, NJ (US); Emery Rose, Astoria, NY (US); Signe M. Lund, Weston, FL (US); Frederic S. Wright, Ardmore, PA (US)

(73) Assignee: Exogen, Inc., Piscataway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/420,274

(22) Filed: Oct. 18, 1999

(65) Prior Publication Data

US 2002/0032393 A1 Mar. 14, 2002

Related U.S. Application Data

(63) Continuation of application No. PCT/US98/07532, filed on Apr. 16, 1998.
(60) Provisional application No. 60/044,710, filed on Apr. 18, 1997.

(51) Int. Cl.[7] .............................................. A61B 17/56
(52) U.S. Cl. ........................................................ 601/2
(58) Field of Search ...................... 601/2, 3, 4; 600/439, 600/459; 310/311, 322, 334, 340

(56) References Cited

U.S. PATENT DOCUMENTS

| 4,183,249 | A | * | 1/1980 | Anderson ..................... 73/626 |
| 4,440,025 | A | | 4/1984 | Hayakawa et al. |
| 4,530,360 | A | | 7/1985 | Duarte |
| 4,792,336 | A | | 12/1988 | Hlavacek et al. |
| 4,802,477 | A | | 2/1989 | Gabbay |
| 5,139,498 | A | | 8/1992 | Astudillo Ley |
| 5,163,598 | A | | 11/1992 | Peters et al. |
| 5,330,489 | A | | 7/1994 | Green et al. |
| 5,520,612 | A | | 5/1996 | Winder et al. |
| 5,524,624 | A | | 6/1996 | Tepper et al. |
| 5,762,616 | A | | 6/1998 | Talish |
| 5,775,328 | A | * | 7/1998 | Lowe et al. ............ 128/662.06 |
| 5,844,140 | A | * | 12/1998 | Seale .......................... 73/633 |
| 5,904,659 | A | * | 5/1999 | Duarte et al. .................. 601/2 |
| 6,190,336 | B1 | * | 2/2001 | Duarte et al. .................. 601/2 |

FOREIGN PATENT DOCUMENTS

| EP | 0695559 | 2/1996 |
| WO | WO 95/03744 | 2/1995 |

\* cited by examiner

Primary Examiner—Marvin M. Lateef
Assistant Examiner—Eleni Mantis Mercader
(74) Attorney, Agent, or Firm—Bruce D. Gray; Kristin L. Johnson; Kilpatrick Stockton LLP

(57) ABSTRACT

Ultrasound application devices and methods of use for sternum healing of a patient includes the steps of positioning an ultrasound application device near a sternum having approximated portions, and applying ultrasound to the approximated portions for promoting healing. The ultrasound application device includes a transducer for generating the ultrasound, and a base for positioning the transducer near to the sternum. A diverging lens may be disposed between the transducer and the sternum for acoustically diverging the ultrasound to flood the sternum with ultrasound. A plurality of transducers may be included in a plurality of recesses of the base along a longitudinal length of the sternum for applying the ultrasound along the longitudinal length of the sternum. A ring may be included to be positioned and secured about the neck of the patient. The ring may be woven as and/or incorporated in a tie. A metal strip may be used which responds to signals from the transducer for generating the ultrasound applied to the sternum. The metal strip may be implanted within the patient substantially adjacent to the sternum. Also, the ultrasound application device may operate in conjunction with a mesh implanted in the patient substantially adjacent to the sternum.

34 Claims, 9 Drawing Sheets

ULTRASOUND APPLICATION DEVICE FOR ACCELERATING STERNUM HEALING

This is a continuation of application Ser. No. PCT/US98/07532 filed Apr. 16, 1998 which claims the benefit of provisional application No. 60/044,710 filed Apr. 18, 1997.

BACKGROUND INFORMATION

1. Technical Field

This disclosure relates to therapeutic medical applications of ultrasound, and in particular to a method for promoting healing of the sternum using therapeutic ultrasound.

2. Description of the Related Art

Referring to FIG. 1, the sternum 10 is a heavily vascularized tissue positioned in the chest 12 between the lateral sets of ribs 14, 16 forming the rib cage. Being composed of both bone and cartilage and heavily vascularized, the sternum 10 has unique characteristics with respect to the skeletal structure of humans.

During conventional open heart surgery, the sternum is typically cut, as shown in FIG. 2, by a saw or by an electrocautery device to separate and spread the rib cage open to expose the heart, as shown in FIG. 3. The cut 18 is generally positioned longitudinally along the length of the sternum 10 for maintaining the conjunction of the portions 20, 22 of the sternum 10 with the respective sets of ribs 14, 16.

When the sternum is cut in such surgical procedures, the resultant bleeding from the sternum may be significant due to its heavy vascularization. Typically, the bleeding is stopped during the surgery by cautery procedures or by application of bone wax; i.e. wax or wax-like substances for sealing the cut and severed blood vessels.

After completion of the surgical procedure, the chest cavity is closed, which involves positioning and re-approximating the portions of the cut sternum together for subsequent healing, using, for example, stainless steel wires 24–28 and/or bands, as shown in FIG. 4, for affixing the sternum portions 20, 22 together and/or for constricting the patient's chest to force the sternum portions to be adjacent. For example, U.S. Pat. Nos. 4,802,477 and 5,330,489 disclose sternum closure devices for retaining split portions of human tissue such as the sternum in adjacent contacting relation to promote healing. Other devices or structure may be used to secure the sternum portions together during healing; for example, U.S. Pat. No. 5,163,598 describes a sternum stapling apparatus for stapling the sternum portions together with a bone staple.

U.S. Pat. No. 5,139,498 describes a device consisting of a plate having two flat longitudinal parallel anchoring members with through-holes for threading wire to hold the sternum portions together. U.S. Pat. No. 4,792,336 describes a surgical repair device composed of absorbable material which is braided and used for securing tissue together. U.S. Pat. Nos. 4,792,336 and 5,139,498 are incorporated herein by reference.

Such devices described above may be disposed adjacent to the approximated sternum portions and internally located after the patient's chest is closed and sutured. Such devices may be permanent or may be removed at a later date after the sternum healing has been sufficiently effected.

Post-operative complications to the union of the sternum portions may be caused due to the cautery or bone wax which, in stopping the bleeding during the surgery, prevent proper healing after the surgery. Other causes of post-operative complications of the cut sternum include ventilation of the chest cavity; i.e. breathing. Due to the position of the sternum between the ribs and over the chest, breathing causes stress and strain on the sternum portions, preventing proper healing.

In addition, as the muscles of the chest are connected to other muscles such as those to the abdomen, upper limbs, and head, muscular movement also may contribute stress and strain on the sternum portions during healing.

Furthermore, known devices such as wires and bands as well as plates and muscle clamps have been used to secure the sternum portions together. The use of these devices have met with some success to promote healing of the sternum. However, such devices have been found to loosen, such as wire 26, and even migrate, such as wire 28, thus allowing the sternum portions 20, 22 to separate, as illustrated in FIG. 4.

Accordingly, the incidence of dehiscence of the sternum; i.e. the failure of the sternum to heal, which results or causes relatively massive infection to the sternum and surrounding region, is of significant concern. In turn, such infections further reduce the healing of the sternum by reducing the ability of the sternum portions to join and fuse to each other during proper healing.

Further, due to movement of the sternum portions 20, 22 caused by muscular activity and breathing, as well as strain to the spinal joints and intercostal joints 30, 32, shown in FIG. 4, from the separation of the ribs, in addition to nerve exposure due to the surgery, serious pain may occur from even regular activity and movement.

It is generally known that complications from such heart surgery and post-operative effects, such as dehiscence of the sternum, may occur at a frequency of about 0.5% to about 7.0% of patients undergoing such heart surgery. Of such patients experiencing complications, mortality occurs in about 14% of such cases.

Post-operative complications associated with the failure of the sternum to heal properly are generally most common among the elderly, diabetics, obese people, smokers, people who have used steroids, patients having chemotherapy or radiation therapy, and patients who have lung disease or lung surgery. In particular, for the elderly who may more often require heart, lung, or other chest surgery, complications in sternum healing generally have an increased likelihood since the sternum is about 1 cm to about 1.5 cm. thick, but such thickness reduces in relation to one's age.

Although known devices are indeed effective for promoting healing of a cut sternum, the frequency of complications and mortality is still considerable. In addition, such devices are limited in effectiveness, as the sternum portions may separate despite such devices, or in fact because such devices may not operate properly. For example, a bone staple holding the sternum portions together may loosen due to the natural and regular breathing and other muscular movement of the sternum and ribs. Further, such known devices for sternum healing may require replacement or adjustment to compensate for any maladjustment or ineffectiveness.

Accordingly, a need exists for promoting effective sternum healing; for example, a device and/or a method which heals the sternum, individually or in conjunction with such devices known in the art, including wires and bands.

A need also exists for a device and/or a method for promoting sternum healing which is conveniently applied, and which may be applied with less expense. Such a device and/or method may also be non-invasive, to allow recovering patients to avoid additional surgery to replace or adjust known sternum healing devices and methods.

The application of ultrasound to accelerate the healing of tissue and bone has been described, for example, in commonly assigned U.S. Pat. No. 4,530,360 to Duarte and U.S. Pat. No. 5,520,612 to Winder et al. For example, as described by the Duarte patent, ultrasound may be applied to bone, with ultrasonic frequencies of about 1.5 MHz with pulse widths which vary between 10 $\mu$s and 2,000 $\mu$s, and with pulse repetition rates which vary between 100 and 1,000 Hz. Such applications of ultrasound have been shown to accelerate the normal healing process of bone fractures, pseudoarthroses, and the like. Heretofore, ultrasound has not been applied to promote the post-operative healing of the sternum.

SUMMARY

It is recognized herein that the application of therapeutic ultrasound to the sternum accelerates the healing of the sternum, and so minimizes dehiscence and other complications of surgery involving cutting of the sternum.

A method for sternum healing of a patient is disclosed which includes the steps of positioning an ultrasound application device substantially adjacent to a sternum having approximated portions; and applying ultrasound to the approximated portions of the sternum for promoting healing of the approximated portions together.

The ultrasound application device includes a transducer for generating ultrasound for application to approximated portions of the sternum for promoting healing of the approximated portions together; and a base for positioning the transducer substantially adjacent to the sternum. In one embodiment, an ultrasound diverging lens is included which is disposed between the transducer and the sternum for acoustically diverging the ultrasound to flood the approximated portions of the sternum for healing thereof.

In another embodiment, a plurality of transducers are included which are positioned in a plurality of recesses of the base along a longitudinal length of the approximated portions of the sternum and substantially adjacent to the skin over the sternum for applying the ultrasound along the longitudinal length of the approximated portions of the sternum.

A ring may be included which is connected to the base and adapted to be positioned and secured about the neck of the patient. The ring may be woven and/or incorporated in a tie.

In another embodiment, a metal strip is included which is operatively connected to the transducer, and which responds to signals from the transducer for generating the ultrasound and for applying the ultrasound to the sternum. The metal strip may be implanted within the patient substantially adjacent to the sternum.

In another embodiment, the ultrasound application device may operate in conjunction with a mesh implanted in the patient substantially adjacent to the sternum, in which the mesh responds to ultrasound applied thereto to promote healing of the sternum.

BRIEF DESCRIPTION OF THE DRAWINGS

The features of the disclosed sternum healing apparatus and method will become more readily apparent and may be better understood by referring to the following detailed description of illustrative embodiments of the present invention, taken in conjunction with the accompanying drawings, in which.

DESCRIPTION OF THE PREFERRED EMBODIMENTS

Figure 1:
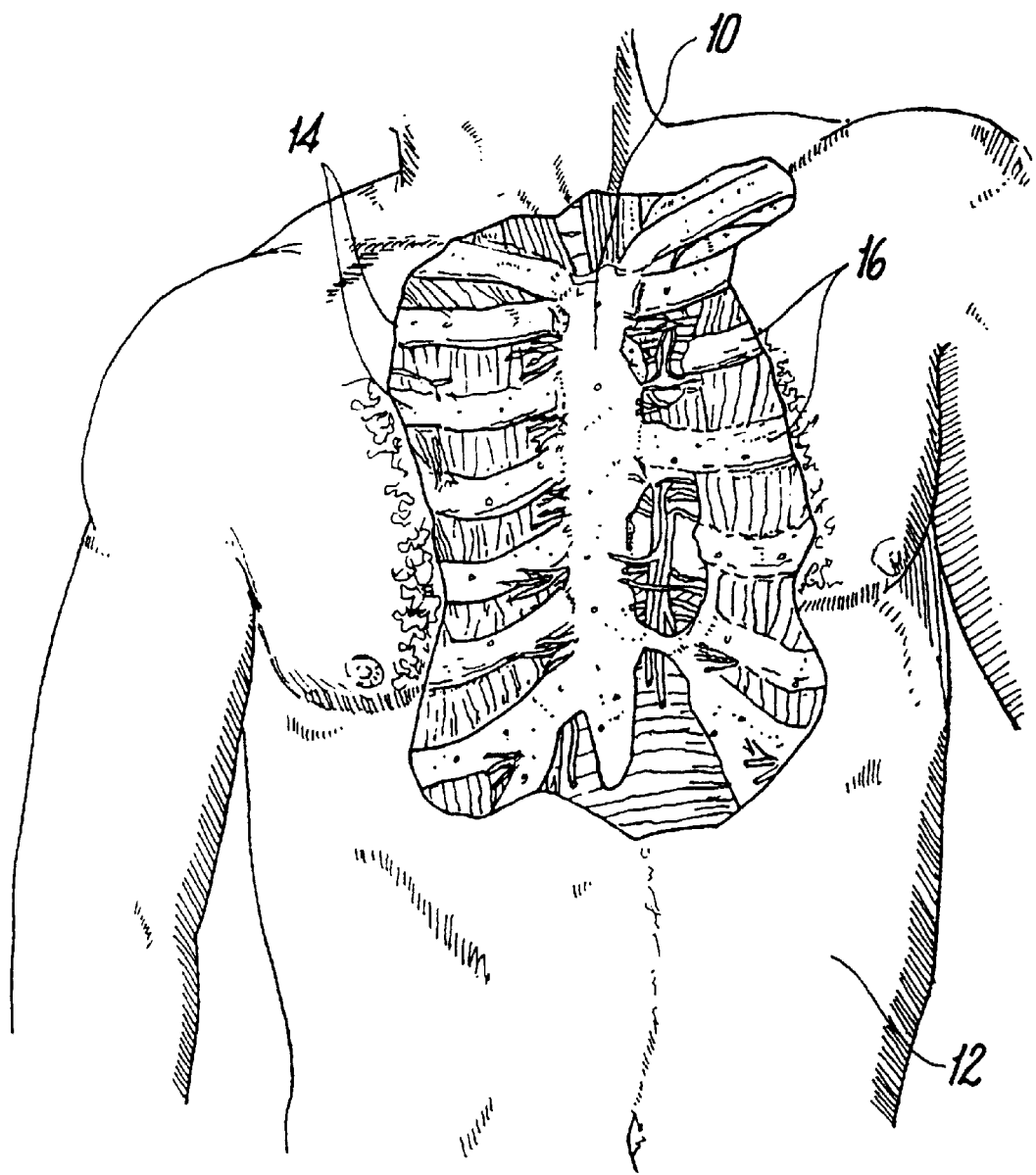
FIG. 1 is a diagram of the sternum and chest cavity.
Figure 2:
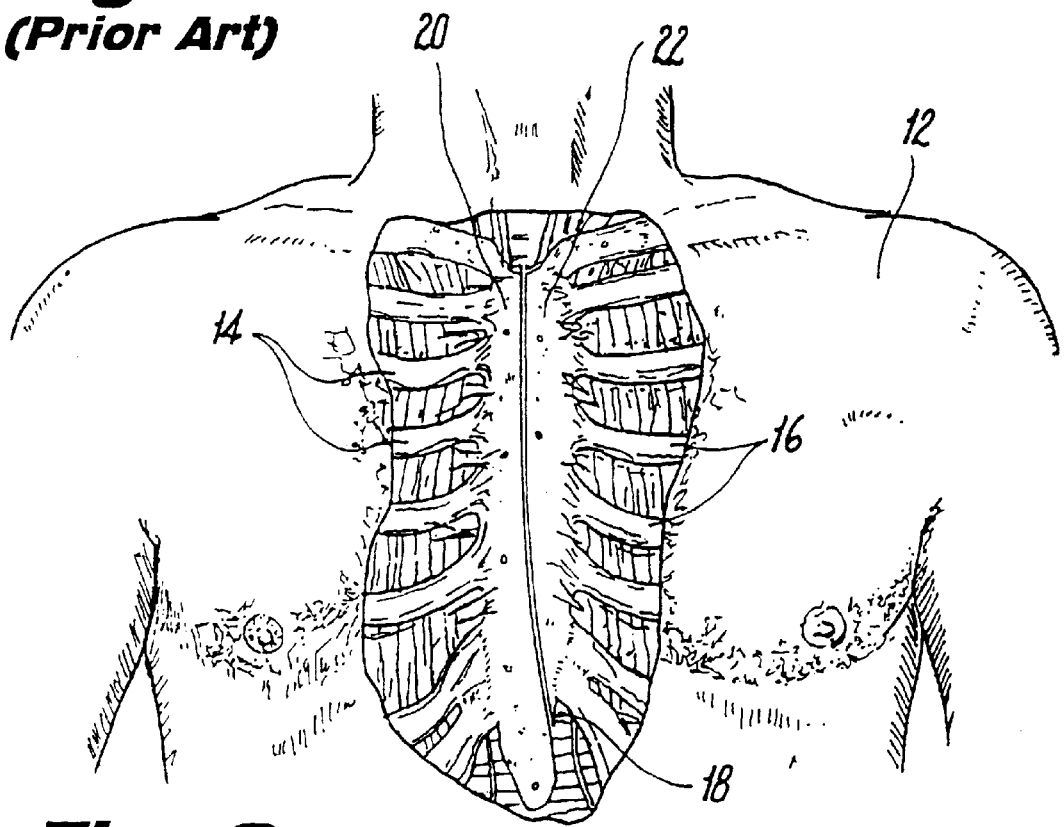
FIG. 2 is a diagram of the sternum having a cut therethrough.
Figure 3:
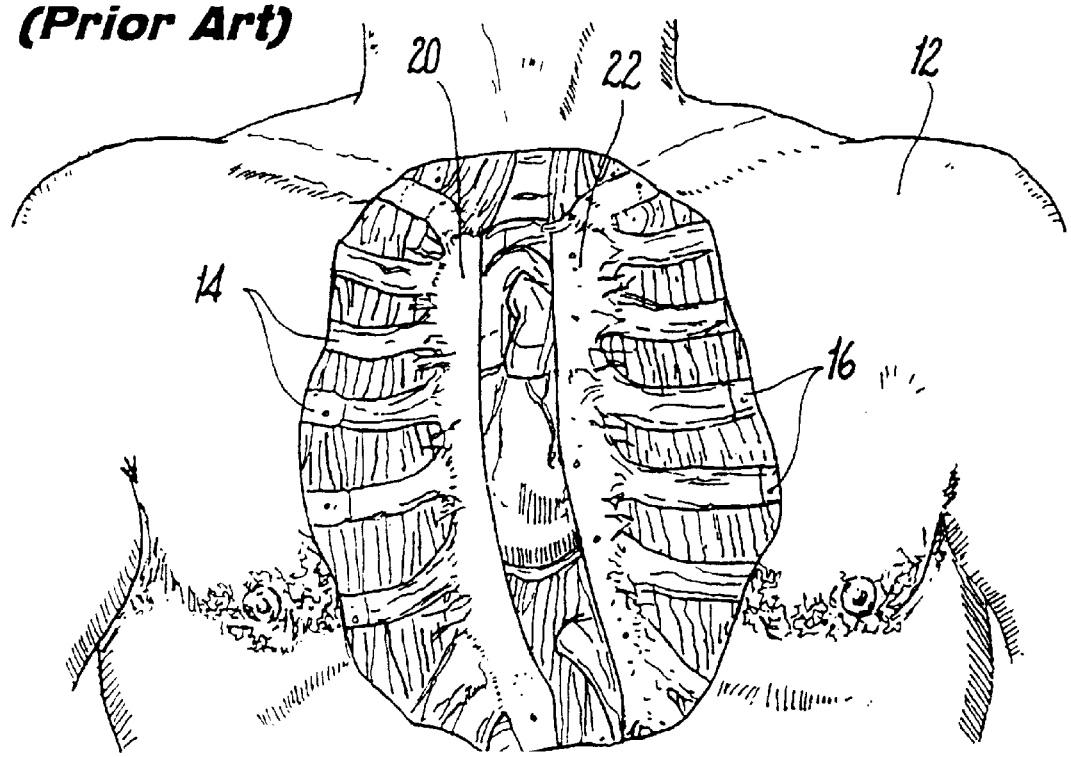
FIG. 3 is a diagram of the cut sternum and associated ribs being separated.
Figure 4:
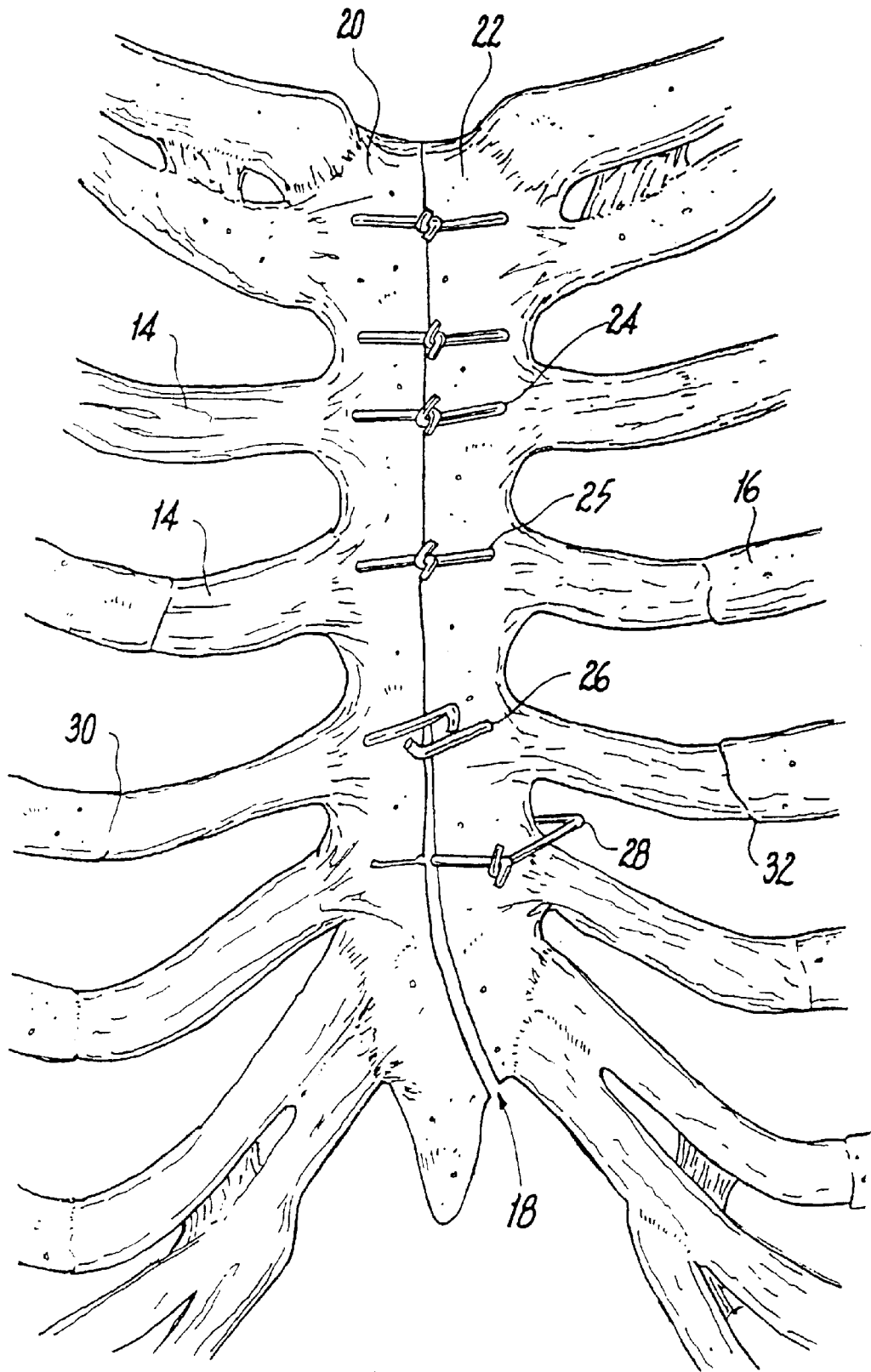
FIG. 4 is a diagram of a cut sternum having portions thereof approximated using wires.

Referring now in specific detail to the drawings, with like reference numerals identifying similar or identical elements, as shown in FIGS. 3–15, the present disclosure describes various apparatus and methods for applying ultrasound to promote healing of a cut sternum. The term "cut sternum" is herein defined to be a sternum which has been apportioned into separable portions by a saw, by an electrocautery device, and/or by other devices and methods known in the art. In this disclosure, for illustrative purposes, the sternum 10 is shown, for example, in FIG. 1, as having been cut into two portions 20, 22 of substantially equal size, and may be referred to as "sternum halves". However, it is to be understood that the relative sizes of the portions 20, 22 of the sternum 10 may be of any proportion.

Figure 5:
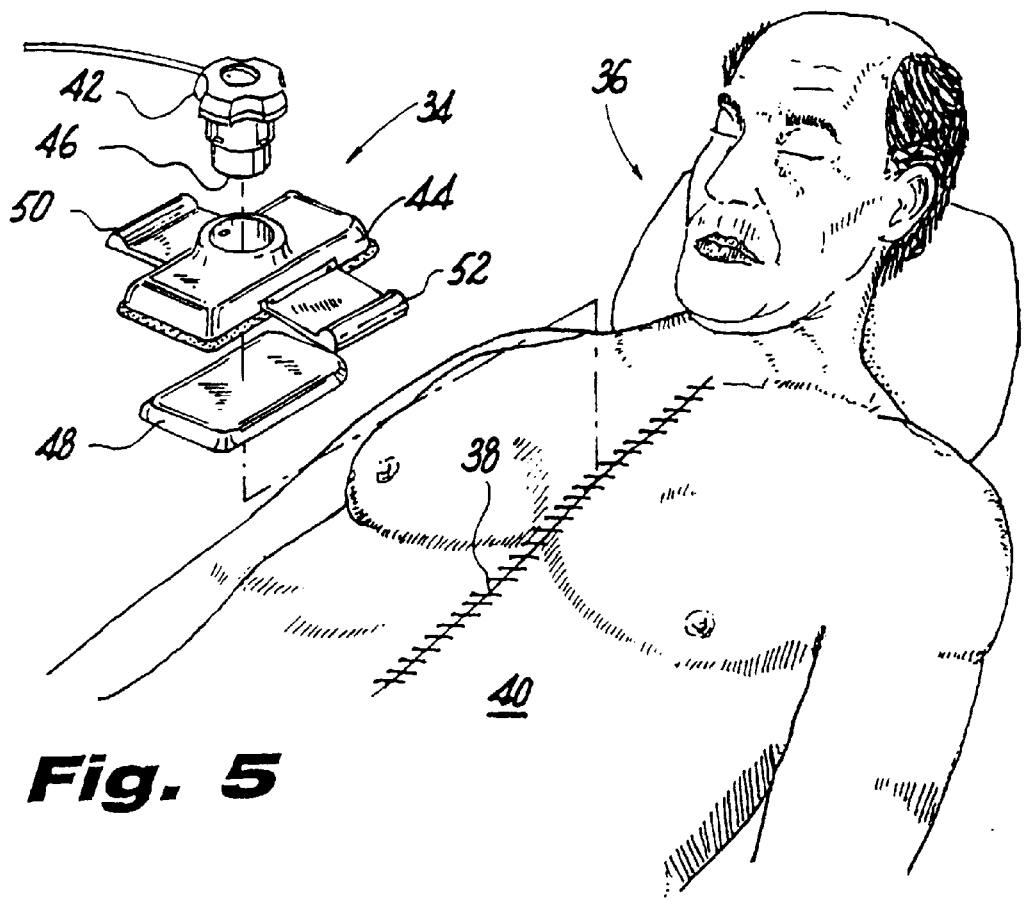
FIGS. 5–6 are diagrams of one embodiment of the application of ultrasound to the cut sternum using a diverging lens.
Figure 6:
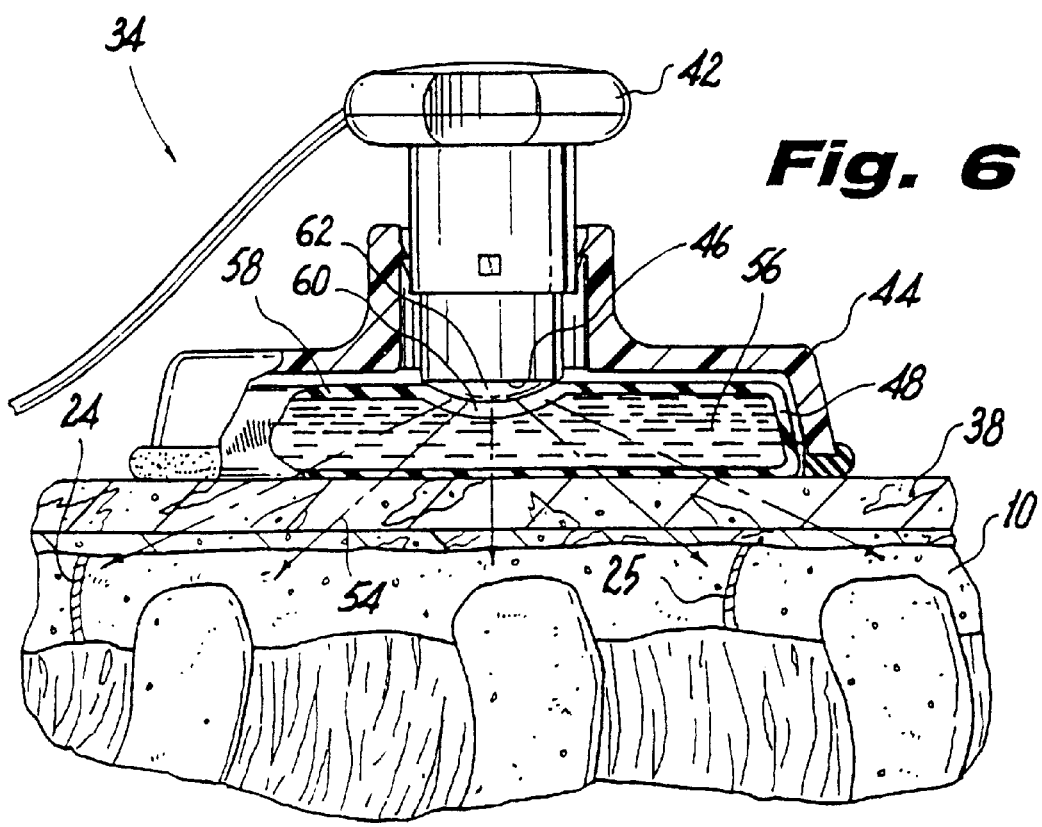

As shown in an illustrative embodiment in FIGS. 5–6, the disclosed apparatus and method includes an ultrasound application device 34 for use with a patient 36 after surgery in which the patient's sternum 10 has been cut and then the portions 20, 22 thereof are approximated. The ultrasound application device 34 is positioned substantially adjacent to the skin 38 of the closed chest cavity 40 in which the cut portions 20, 22 of the sternum 10 are approximated as shown, for example, in FIG. 4. The ultrasound application device 34 includes a transducer 42 operatively connected, for example, by a wire to a power source for generating ultrasound. The transducer 42 is disposed in a transducer support housing 44, and has a transmission end 46 which is positioned substantially adjacent to an ultrasonic diverging lens 48, described in detail below, which may be an ultrasound conductive pad, such as a gel pad.

The transducer 42 includes or is operatively connected to ultrasound generation circuitry known in the art, such as the transducer and acoustic system described in U.S. Pat. No. 5,520,612 to Winder et al., which is incorporated herein by reference. In an illustrative embodiment, the transducer 42 is connected to an ultrahigh-frequency generator, a low-frequency signal generator, and a modulator connected to these generators for supplying pulse-modulated ultrahigh-frequency signals to the transducer 42.

In general, an ultrasound carrier frequency between 250 kHz and 10 MHz coupled with a relatively low-frequency modulating signal (e.g. 5 Hz to 10 kHz) and low intensity acoustic signal (e.g. less than 100 milliwatts/cm$^2$) aids, and will be effective for therapeutic treatment.

The transducer support housing 44 may be configured to be stable when positioned on the closed chest cavity 40 of the patient 36, such as a reclining patient, during a session of ultrasonic therapy. In an illustrative embodiment, the transducer support housing 44 includes or is attached to weighted panels 50, 52 for weighing down the ultrasonic application device 34 during the ultrasonic therapy. Alternatively, the transducer support housing 44 may include or be attached to a band or other apparatus for securing the ultrasonic application device 34 substantially adjacent to the closed chest cavity 40.

As shown in FIG. 6, the ultrasonic application device 34 is positioned substantially adjacent to the skin 38 above the sternum 10 for healing thereof, in which the sternum 10 has portions approximated by wires 24, 25 or, alternatively, other mechanisms for approximating the sternum portions. In the illustrative embodiment, the transducer support housing 44 may include a recess for positioning the ultrasonic diverging lens 48 therein such that ultrasonic waves 54 from the transmission end 46 of the transducer 42 are conveyed through the skin 38 to the sternum 10 to accelerate the healing thereof.

In the illustrative embodiment, the ultrasonic diverging lens 48 may be a pad, bladder, or other structure which is substantially conductive of ultrasound and which is adapted to acoustically diverge such ultrasonic waves 54 from the transmission end 46 of the transducer 42. For example, the ultrasonic diverging lens 48 may be an enclosed structure for retaining ultrasound conductive gel 56 which transmits ultrasound therethrough with relatively low dissipation. In the illustrative embodiment shown in FIG. 6, a top surface 58 of the ultrasonic diverging lens 48 may include a detent 60, which may be curved or indented at an angle, to form a pocket 62 for air or other substances between the detent 60 and the transmission end 46. The curved or indented shape of the detent 60 and the associated shape of the pocket 62, and optionally the conductive properties of the air or substances therein, acts as an ultrasonic lens which spreads or diverges the ultrasonic waves 54 over a greater range than the range due to typical dissipation of ultrasound through gel pads.

Such diverging ultrasound may thus be applied to a substantial portion of the cut sternum 10 during a single therapy session. In addition, the ultrasonic diverging lens 48 may be positioned over the closed chest cavity 40 and configured to apply the ultrasound substantially directly to the approximate center of the cut sternum 10 to promote healing thereof.

The application of ultrasound to promote healing of tissue and bone has been described, for example, in commonly assigned U.S. Pat. No. 4,530,360 to Duarte and U.S. Pat. No. 5,520,612 to Winder et al., with each of these patents being incorporated herein by reference.

The healing in the central region of the cut sternum may be more beneficial in promoting the overall healing of the sternum than healing of the cut sternum at either end thereof; for example, the central region of the sternum may experience the greatest stress and shear forces due to breathing by the patient. Accordingly, the healing of the central region may be more difficult and so of more importance in receiving the therapeutic ultrasound.

Since the sternum 10 lies along the length of the upper chest cavity and is relatively close to the surface of the skin of the patient, flooding the sternum 10 with ultrasonics waves 54 provides sufficient healing of the sternum 10, and high precision and focussed pinpointing of the ultrasound to a specific location is not required. Accordingly, the intensity of the ultrasound applied is not required to be high, and a shallow penetration of the ultrasound provides effective healing.

In addition, the shallowness of the penetration and the absorption of the ultrasound by the sternum 10 effectively limits the ultrasound from penetrating the underlying heart tissue. In addition, the frequency of the ultrasound may be controlled in a manner known in the art to adjust the shallowness of the penetration of the ultrasound.

The ultrasound may also be applied using the ultrasound application device 34 of FIGS. 5–6 in a manner known in the art; for example, the use of a sweeping carrier frequency of the ultrasound, as described in U.S. Pat. No. 5,520,612 may also be used. In addition, phased arrays of transducers and/or sequential irradiation of the sternum 10 may also effectively promote the healing of the sternum 10.

Since the portions of the sternum 10 are approximated by wires 24, 25, the normal healing of the sternum 10 by such approximation occurs. In applying such ultrasound, the ultrasound application device 34 accelerates the healing of the sternum 10, and so complements the use of the wires 24, 25 or other mechanisms for approximating the portions of the sternum 10.

Figure 7:
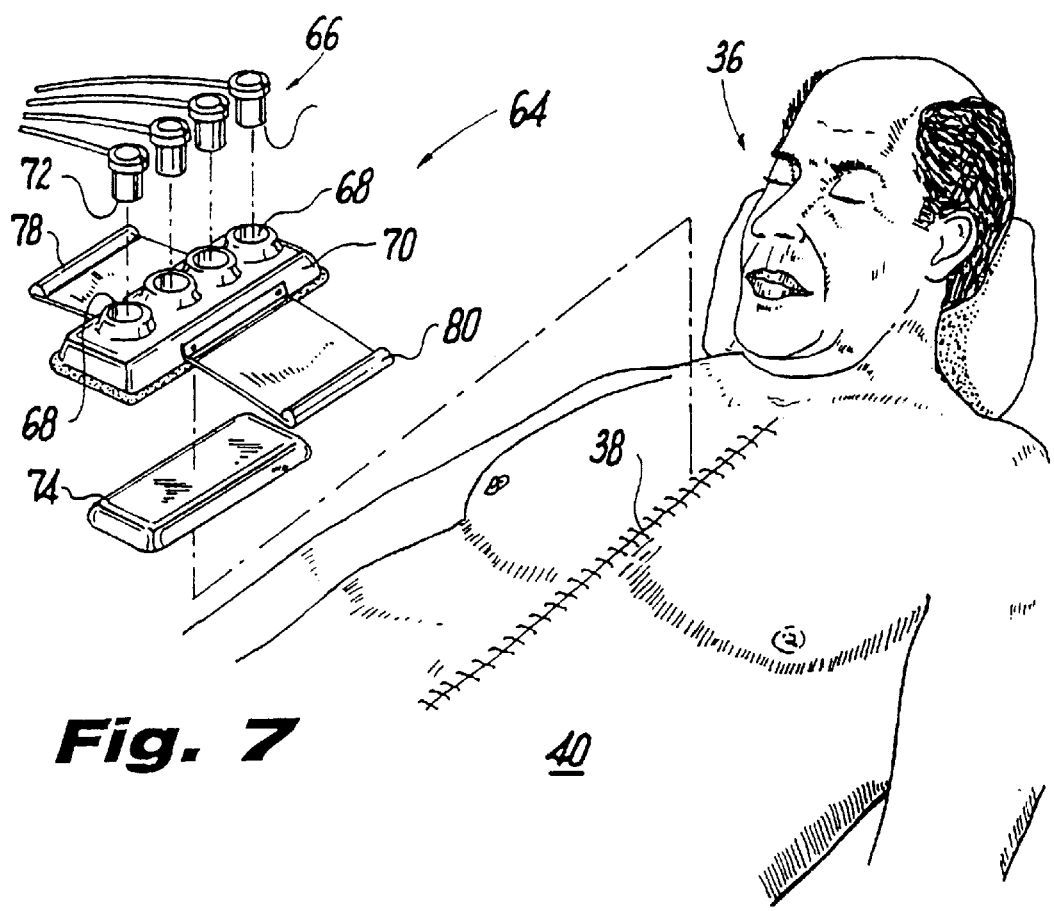
FIGS. 7–8 are diagrams of an alternative embodiment of the application of ultrasound in FIGS. 5–6 using a plurality of ultrasound transducers.
Figure 8:
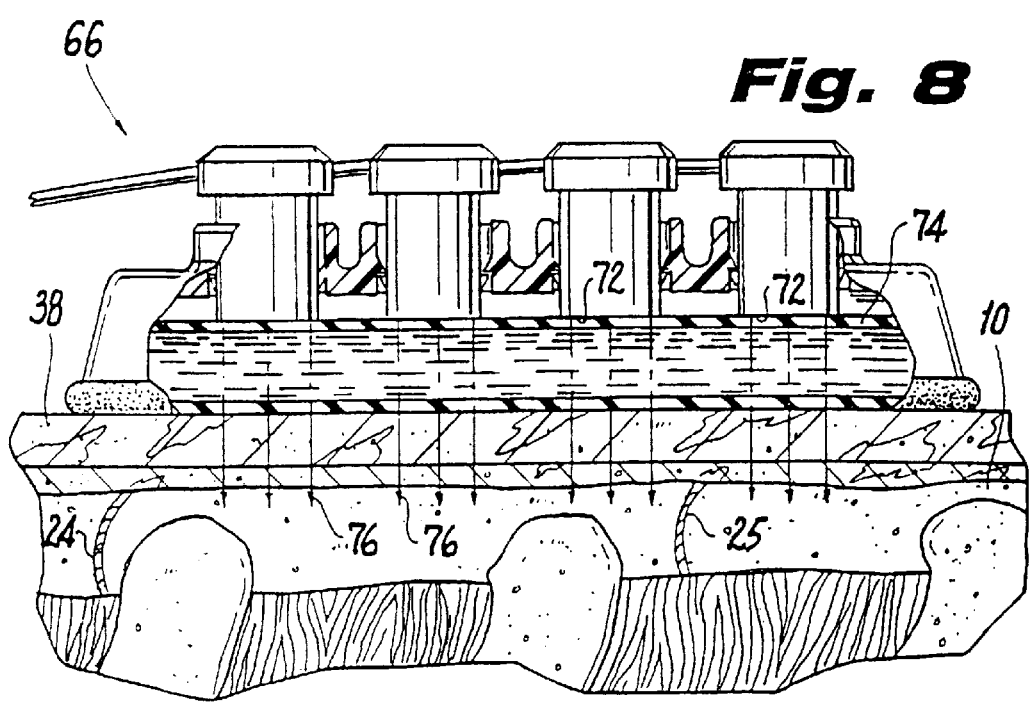

FIGS. 7–8 are diagrams of an alternative embodiment of the application of ultrasound in FIGS. 5–6 for sternum healing. As shown in FIGS. 7–8, the ultrasound application device 64 uses a plurality of ultrasound transducers 66 respectively disposed in corresponding recesses 68 of a transducer support housing 70 such that respective transmission ends 72 of the plurality of transducers may be substantially adjacent to an ultrasonic gel pad 74. The ultrasonic gel pad 74 is positioned substantially adjacent to the skin 38 of the closed chest cavity 40, in which the cut portions 20, 22 of the sternum 10 are approximated by wires 24, 25, as shown, for example, in FIG. 4, so that ultrasonic waves 76 from the plurality of transducers 66 may be directed to the sternum 10 for accelerating the healing thereof.

As described above with reference to FIGS. 5–6, the transducer support housing 70 of FIGS. 7–8 may include or is attached to weighted panels 78, 80 or other devices as described above for positioning the transducer support housing 70 during ultrasonic therapy.

Referring to FIG. 8, in an illustrative embodiment, the plurality of transducers 66 and corresponding transmission ends 72 are oriented to be substantially parallel for transmitting a substantially uniform set of ultrasonic waves 76 through the skin 38 to the sternum 10 for promoting substantially uniform healing is along the longitudinal length of the sternum 10.

In the illustrative embodiments shown in FIGS. 5–8, the ultrasound application devices 34, 64 of FIGS. 5–8, respectively, are used in conjunction with ultrasonic conductive gel pads 48, 74, respectively. In alternative embodiments, it is understood that the ultrasound application devices 34, 64 may also be used with an ultrasound conductive gel spread over the skin 38 substantially adjacent to the sternum 10 for facilitating transmission of the ultrasonic waves through the skin 38 to the sternum 10 for accelerating the healing thereof.

Figure 9:
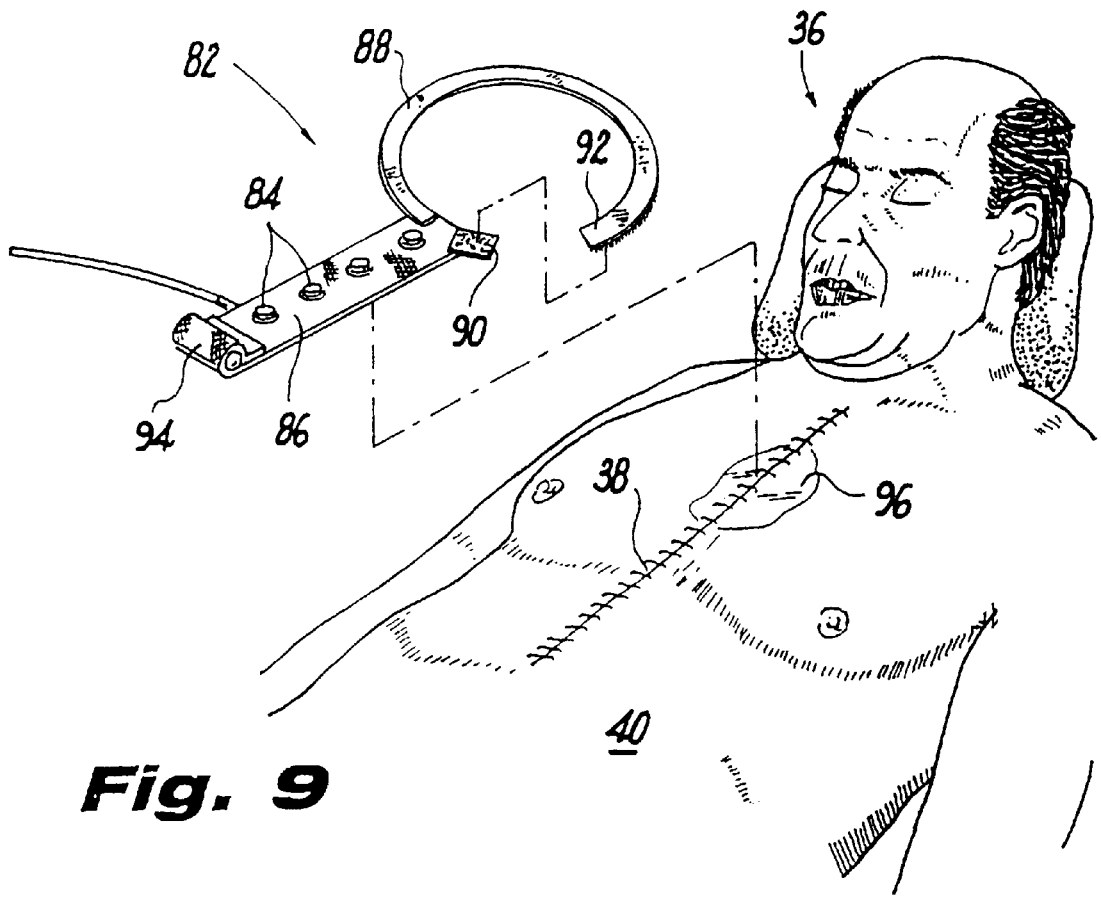
FIGS. 9–10 are diagrams of another embodiment of an ultrasound application device using a set of transducers which may be secured about the neck of the patient.
Figure 10:
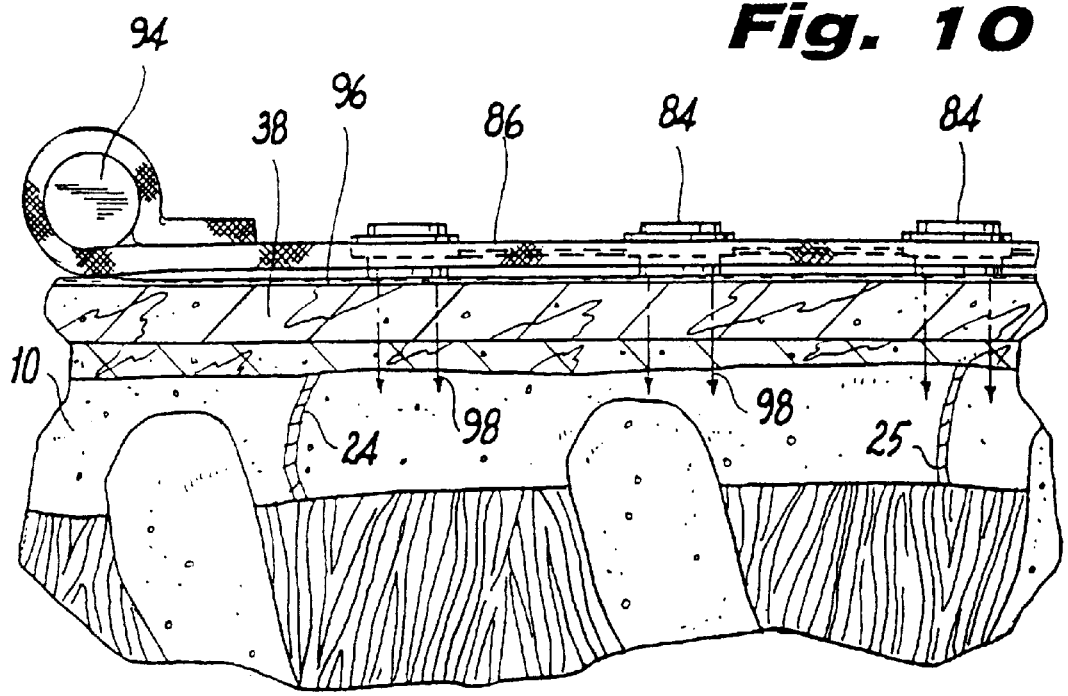

FIGS. 9–10 are diagrams of another embodiment of an ultrasound application device 82 using a set of transducers 84 disposed on a base 86 which is attached to a ring 88 or other structure for securing the ultrasound application device 82 about the neck of the patient 36. In one embodiment, the ring 88 may be an open ring with ends 90, 92 capable of being attached and secured using a clasp or other securing structures, such as hook and link devices using "VELCRO". In other embodiments, the ultrasonic application device 82 may be incorporated into a necktie or other woven material for positioning the ultrasonic application device 82 substantially adjacent to the skin 38 for promoting healing of the sternum 10 during therapy sessions or during regular activities by the patient 36.

The ultrasound application device 82 may also include a weight 94 for minimizing movement of the base 86 due to movement or shifting of the patient 36 during the application of the ultrasound from the set of transducers 84. In the illustrative embodiment shown in FIGS. 9–10, the ultrasound application device 82 may be used in conjunction with an ultrasound conductive gel 96 spread over the skin 38 substantially adjacent to. the sternum 10 for facilitating transmission of the ultrasonic waves 98 through the skin 38 to the sternum 10 for healing thereof. It is understood that, in other embodiments, the ultrasound application device 82 may include or may be used in conjunction with ultrasound conductive gel pads, as described above for FIGS. 5–8.

Figure 11:
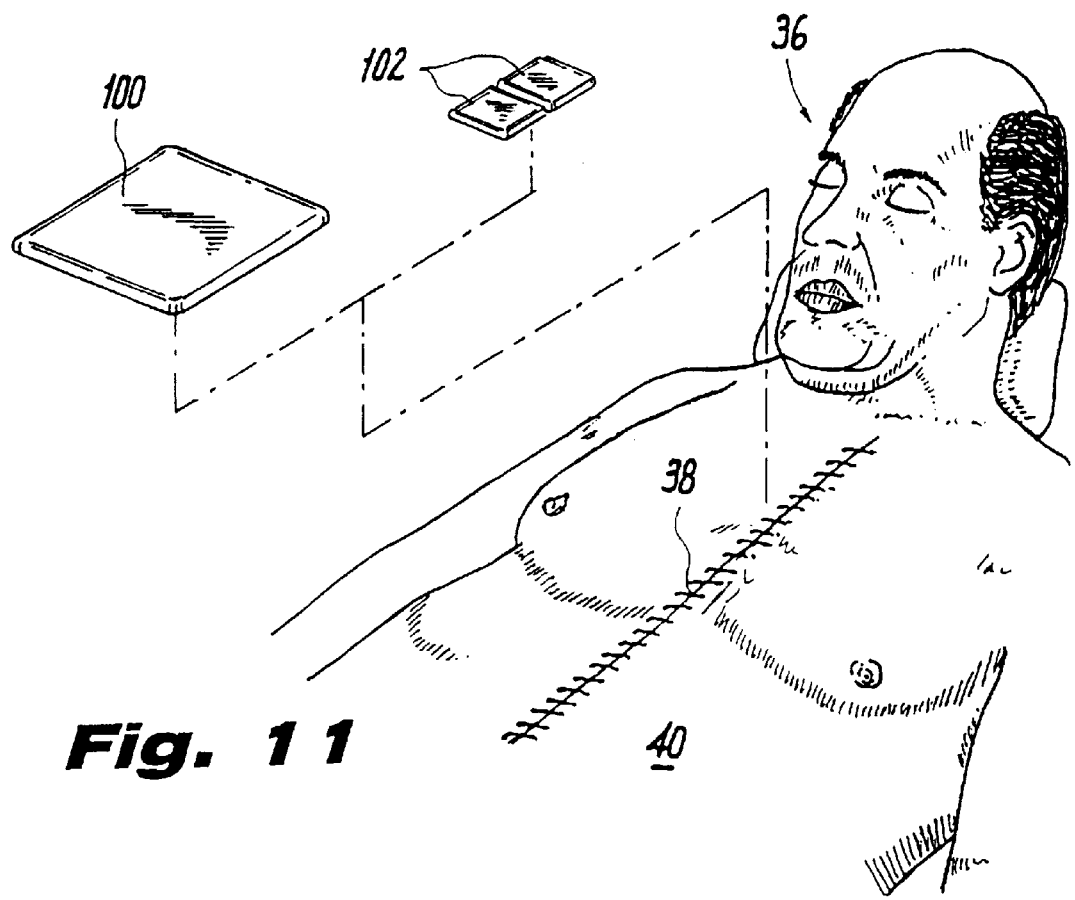
FIG. 11 is a diagram of a sterile pad for use with ultrasound application devices to promote sternum healing.

As shown in FIG. 11, the aforesaid ultrasound application devices of FIGS. 5–10 may be used with a sterile sheet 100 or pad in conjunction with ultrasound conductive gel pads 102, in which the sterile sheet 100 is positioned substantially adjacent to the skin 38. Sterile sheets 100, such as sheets commercially available from ECHO, are placed onto the healing cut in the skin 38 to prevent infection thereof. The sterile sheets 100 may also reduce friction of the skin 38 or discomfort to the patient 36 as the gel pads 102 and ultrasound application devices (not shown in FIG. 11) are positioned on the sterile sheet 100 substantially adjacent to the skin 38 during the ultrasound therapy sessions.

Figure 12:
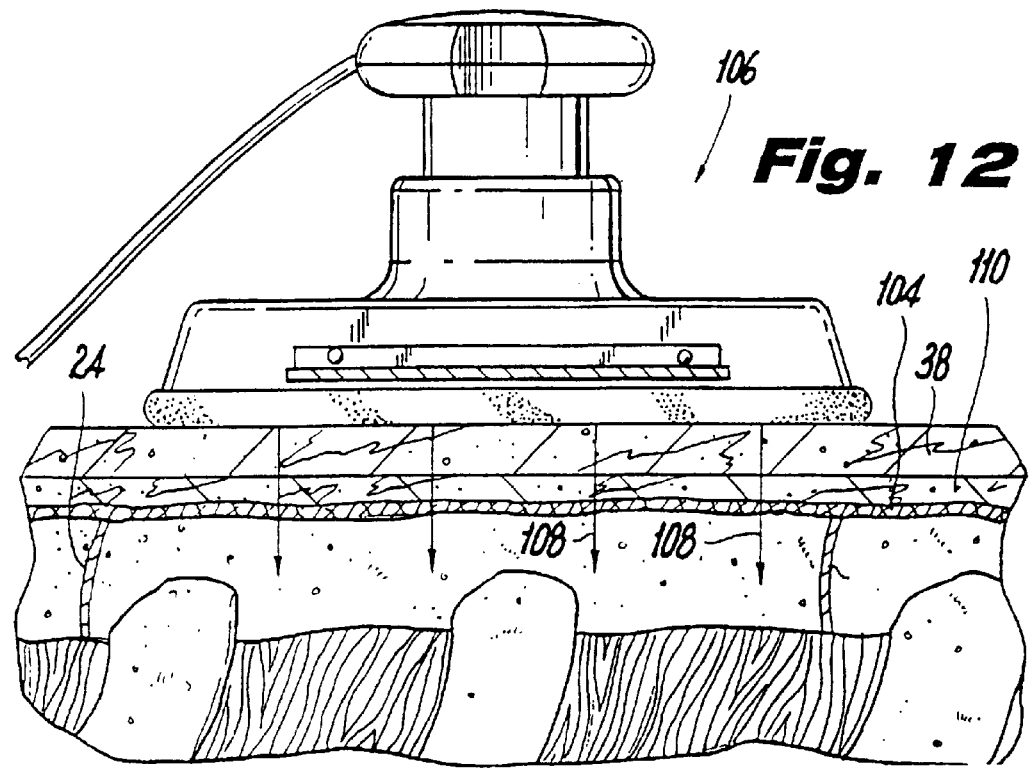
FIG. 12 is a diagram of the use of a mesh in conjunction with an ultrasound application device for applying ultrasound to promote sternum healing.

FIG. 12 is a diagram of the use of a mesh 104 in conjunction with an ultrasound application device 106 for applying ultrasound to promote sternum healing. As shown in FIG. 12, the ultrasound application device 106 may be used in conjunction with an ultrasound conductive gel pad (not shown in FIG. 12) for applying ultrasonic waves 108 through the skin 38 and muscle 110. substantially adjacent to the sternum for accelerating the healing thereof. The ultrasound application device 106 and gel pad used therewith may be any of the embodiments described above for FIGS. 5–10.

The mesh 104 is composed of a woven material which is conductive of ultrasound. During surgery, the mesh 104 is placed in the body of the patient 36 substantially adjacent to the sternum 10 such that, as the ultrasonic waves 108 is transmitted through the skin 38 and the muscle 110, the mesh 104 promotes the application of the ultrasonic waves 108 to the sternum 10 for healing thereof. The mesh 104 may be absorbable with. an absorption rate such that, after the sternum 10 has substantially been healed, the mesh 104 is left in the body of the patient 36 to be absorbed. Alternatively, the mesh 104 may be removed from the patient 36 after sufficient healing of the sternum 10.

Figure 13:
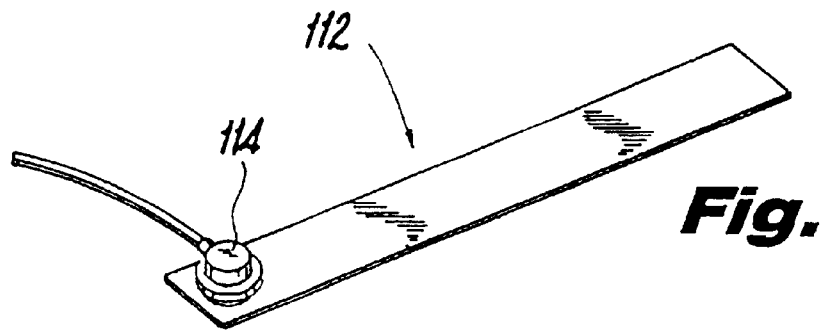
FIG. 13 is a diagram of a metal plate including an ultrasound transducer for applying ultrasound.

In another embodiment, the sternum 10 may be healed by ultrasound using a metal strip or plate. As shown in FIG. 13, the metal strip 112 including a transducer 114 for vibrating the metal strip 112 to generate ultrasound. In one embodiment, shown in FIG. 14, the metal strip 112 may be positioned substantially adjacent to the skin 38 outside of the body of the patient 36 such that the vibrations 116 of the metal strip 112 generate ultrasonic waves 118 which is transmitted through the skin 38 and muscle 110 to heal the sternum 10. An ultrasound conductive gel pad 120 and/or a sterile sheet may also be used in conjunction with the metal strip 112.

By exciting the metal strip 112 at one end using the transducer 114, harmonic changes are induced in the metal strip 112 such that loops and nodes of ultrasound move along the longitudinal length of the metal strip 112. The depth of the penetration of the ultrasonic waves 118 may be controlled in a matter known in the art, such as by using frequency tracking and gain control using pulse echo techniques as well as feedback control techniques.

Since the metals trip 112 is disposed outside the body of the patient 36, the metal strip 112 may be disposable, such as after a single use, or re-usable. In addition, the metal strip 112 may be removably attached to the transducer 114 such that the metal strip 112 is disposable, while the transducer 114 may be re-used.

In an alternative embodiment, the metal strip 112 may be implanted during surgery to be substantially adjacent to and running along the longitudinal length of the sternum 10 under the skin 38 and muscle 110. In another embodiment, the metal strip 112 may be secured to the sternum 10 by the wires 24, 25. As the metal strip 112 is implanted, the implanted metal strip 112 does not require the use of conductive gel pads. Such an implanted metal strip 112 may be used to provide substantially continuous amounts of ultrasonic waves 118 to the sternum 10 for accelerated healing thereof. Accordingly, therapy sessions in which the patient is reclining and relatively immobile during the application of the ultrasound may be reduced or even eliminated.

Figure 14:
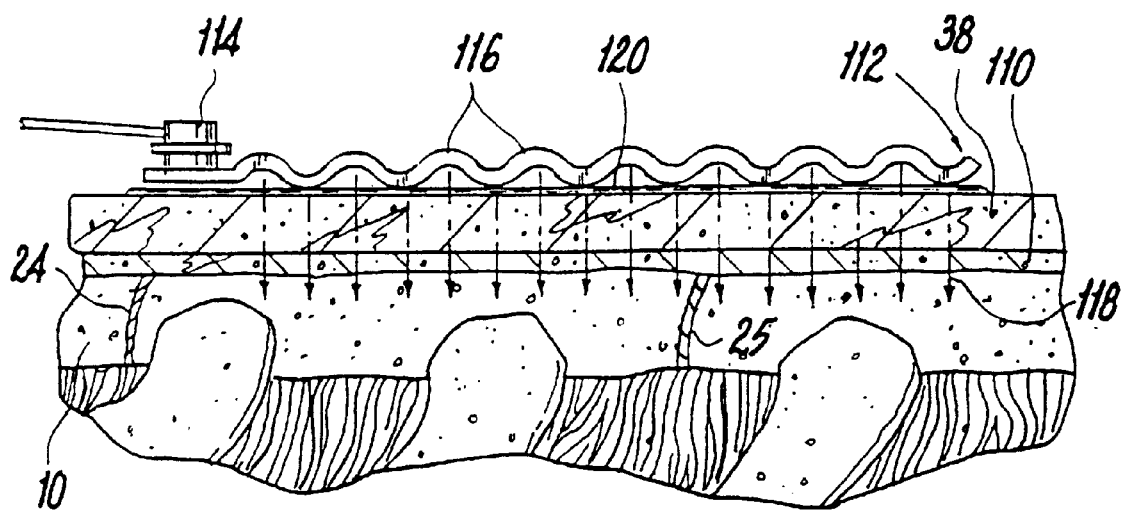
FIGS. 14–15 are diagrams of alternative embodiments of the use of the metal plate of FIG. 13.
Figure 15:
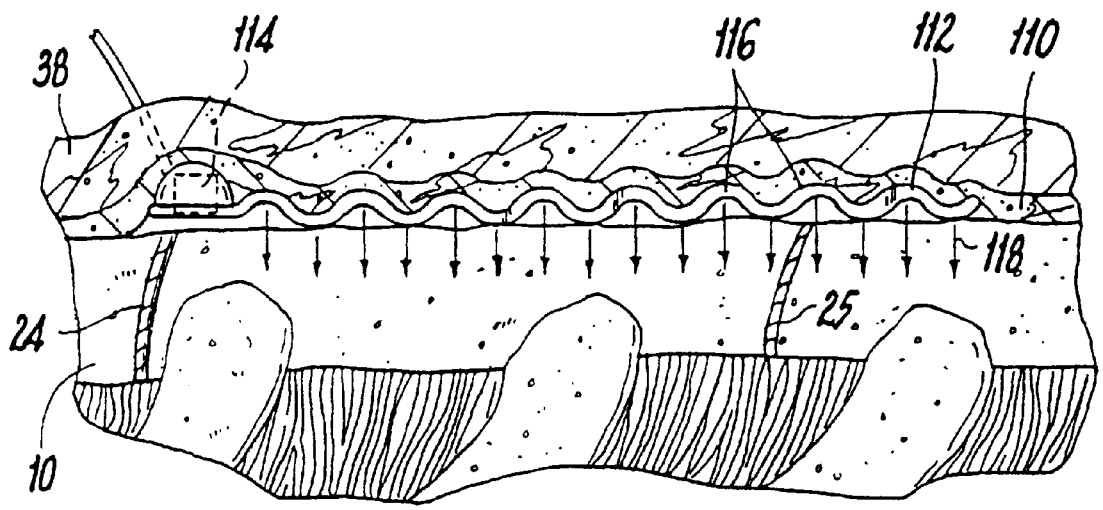

It is to be understood that the vibrations 116 shown in FIGS. 14–15 are exaggerated for illustrative purposes.

Figure 16:
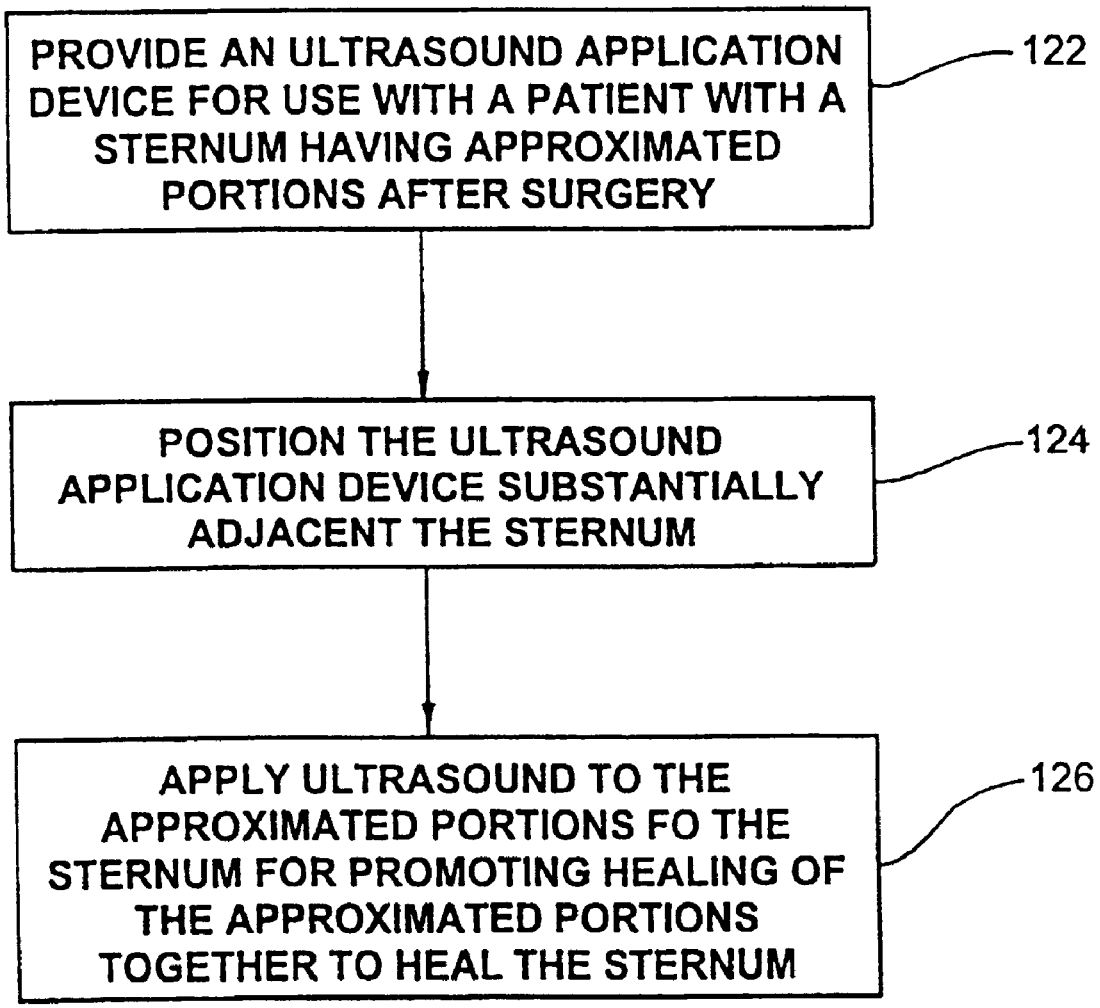
FIG. 16 is a flowchart of a method for healing the sternum.

As described above, the sternum 10 may be healed by the method as shown in FIG. 16, including the steps of providing an ultrasound application device in step 122 for use with a patient with a sternum having approximated portions after surgery, positioning the ultrasound application device substantially adjacent to the sternum 10 in step 124, and applying ultrasound to the approximated portions of the sternum in step 126 for promoting healing of the approximated portions together to heal the sternum.

While the disclosed ultrasound application apparatus and method for sternum healing have been particularly shown and described with reference to the preferred embodiments, it is understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. A method for accelerating sternum healing, comprising:
coupling an ultrasound application device to a tissue surface positioned substantially adjacent to approximated sternum portions using an ultrasound conductive material, wherein the ultrasound application device comprises at least one transducer, and a base coupled with the transducer;
securing the ultrasound application device adjacent the approximated sternum portions using a ring attached to the base and adapted to be positioned about a neck of a patient;

applying ultrasound to the approximated portions of the sternum for promoting healing of the approximated portions by generating ultrasound using the transducer.

2. The method of claim 1, wherein coupling the ultrasound application device further comprises coupling an ultrasound application device comprising a plurality of transducers positioned along a longitudinal length of the approximated sternum portions and substantially adjacent to the tissue surface, and wherein applying ultrasound to the approximated sternum portions further comprises generating ultrasound using the plurality of transducers and applying the ultrasound along the longitudinal length of the approximated sternum portions.

3. The method of claim 1, further comprising positioning a sterile sheet between the transducer and the sternum for healing the sternum.

4. The method of claim 1, wherein securing the ultrasound application device further comprises positioning a ring comprising an opening, a first end and a second end, around the neck of the patient so that the neck is at least partially located in the opening and attaching the first end to the second end in order to prevent the ring from moving during therapy.

5. An ultrasound application device, comprising:
a base capable of being positioned adjacent to approximated sternum portions of a patient;
at least one transducer coupled to the base for generating ultrasound for application to approximated sternum portions for promoting healing of the approximated sternum portions together; and
a ring connected to the base and adapted to be positioned and secured about the neck of the patient.

6. The ultrasound application device of claim 5, wherein the at least one transducer comprises a plurality of transducers and wherein the base comprises a plurality of recesses for receiving the plurality of transducers and positioning the plurality of transducers along a longitudinal length of the base so that ultrasound can be applied along a longitudinal length of the approximated sternum portions.

7. The device of claim 5, wherein the ring comprises an opening, a first end and a second end, and wherein the first end is capable of being attached to the second end to secure the base and the at least one transducer about the neck.

8. The ultrasound application device of claim 5, further comprising at least one weighted panel for immobilizing the ultrasound application device relative to the approximated sternum portions during therapy.

9. The ultrasound application device of claim 5, further comprising a sterile sheet positioned between the transducer and the sternum for healing the sternum.

10. The ultrasound application device of claim 5, further comprising a mesh member capable of being implanted in the patient substantially adjacent to the sternum, wherein the mesh member can receive ultrasound generated by the transducer and can transmit the ultrasound to promote healing of the sternum.

11. An ultrasound application system for accelerating sternum healing, comprising:
an ultrasound application device, comprising:
a base capable of being positioned substantially adjacent to approximated sternum portions of a patient; and
a transducer coupled to the base for generating ultrasound for application to approximated sternum portions for promoting healing of the approximated sternum portions;
an ultrasound diverging lens that is coupled to the ultrasound application device and comprises a surface for coupling with a tissue surface positioned substantially adjacent to the approximated sternum portions of a patient for acoustically diverging ultrasound applied to the approximated sternum portions for healing; and
a mesh member capable of being implanted in a patient substantially adjacent to the sternum, wherein the mesh member can receive ultrasound generated by the transducer and can transmit the ultrasound to promote healing of the sternum.

12. The device of claim 11, wherein the ultrasound diverging lens comprises a gel pad.

13. The device of claim 11, wherein the ultrasound diverging lens comprises a coating of conductive gel.

14. The ultrasound application system of claim 11, wherein the mesh member is absorbable by the patient.

15. An ultrasound application device for accelerating sternum healing, comprising:
a transducer for generating ultrasound for application to approximated sternum portions for promoting healing of the approximated sternum portions; and
a metal strip coupled with the transducer for receiving ultrasound generated by the transducer and for transmitting the ultrasound.

16. The ultrasound application device of claim 15, wherein the metal strip is capable of being implanted within a patient substantially adjacent to the sternum.

17. The ultrasound application device of claim 15, wherein the metal strip is disposable.

18. The ultrasound application device of claim 15, wherein the metal strip is releasably coupled to the transducer.

19. An ultrasound application system for accelerating sternum healing, comprising:
an ultrasound application device, comprising:
a base capable of being positioned adjacent to approximated sternum portions of a patient;
at least one transducer coupled to the base for transmitting ultrasound to the approximated sternum portions for promoting healing of the approximated sternum portions; and
an ultrasound diverging lens comprising a first surface for coupling to the ultrasound application device and a second surface for coupling with a tissue surface positioned substantially adjacent to the approximated sternum portions wherein, the first surface comprises a detent that forms a pocket between the ultrasound diverging lens and the ultrasound application device when the diverging lens and the ultrasound application device are coupled.

20. The ultrasound application system of claim 19, wherein the detent comprises a curved surface.

21. The ultrasound application system claim 19, wherein the ultrasound application device further comprises at least one weighted panel for immobilizing the ultrasound application device relative to the approximated sternum portions during therapy.

22. The ultrasound application system of claim 19, further comprising a sterile sheet positioned between the ultrasound application device and the sternum for healing the sternum.

23. The ultrasound application device of claim 19, further comprising a mesh member capable of being implanted in a patient substantially adjacent to the approximated sternum portions, wherein the mesh member can receive ultrasound generated by the transducer and can transmit the ultrasound to promote healing of the sternum.

24. The ultrasound application system of claim 23, wherein the mesh member is absorbable by the patient.

25. The ultrasound application system of claim 19, wherein the ultrasound diverging lens comprises a gel pad.

26. A method for accelerating sternum healing, comprising:
positioning an ultrasound application device substantially adjacent to approximated sternum portions of a patient, wherein the ultrasound application device comprises a transducer operatively engaged with a metal strip; and
applying ultrasound to the approximated portions of the sternum by generating ultrasound with the transducer and transmitting the ultrasound through the metal strip for promoting healing of the approximated portions.

27. The method of claim 26, wherein positioning the ultrasound application device comprises positioning the metal strip on an external tissue surface of the patient and positioning an ultrasound conductive material between the approximated sternum portions and the metal strip.

28. The method of claim 26, wherein positioning the ultrasound application device comprises implanting the metal strip within the patient substantially adjacent to the approximated sternum portions of the sternum.

29. The method of claim 28, further comprising securing the metal strip to the sternum using wires.

30. A method for accelerating sternum healing, comprising:
coupling an ultrasound application device to a tissue surface substantially adjacent to approximated sternum portions, wherein the ultrasound application device comprises:
a base; and
at least one transducer coupled with the base;
coupling an ultrasound diverging lens to the ultrasound application device;
coupling the ultrasound diverging lens with the tissue surface for acoustically diverging the ultrasound to flood the approximated sternum portions for healing;
implanting a mesh member within a patient substantially adjacent to the sternum; and
applying ultrasound to the mesh member and to the approximated portions of the sternum by transmitting ultrasound through the transducer and the ultrasound diverging lens.

31. The method of claim 30, further comprising removing the mesh member after the approximated portions of the sternum have healed.

32. A method for accelerating sternum healing, comprising:
coupling an ultrasound application device to a tissue surface of a patient substantially adjacent to approximated sternum portions, wherein the ultrasound application device comprises:
a base; and
at least one transducer coupled with the base;
coupling an ultrasound diverging lens to the ultrasound application device, wherein the ultrasound diverging lens comprises a first surface positioned adjacent the ultrasound application device and comprising a detent that forms a pocket between the ultrasound diverging lens and the ultrasound application device when the ultrasound diverging lens and the ultrasound application device are coupled; and
applying ultrasound generated by the transducer to the approximated portions of the sternum.

33. The method of claim 32, further comprising positioning a sterile sheet between the ultrasound application device and the tissue surface.

34. The method of claim 32, further comprising implanting a mesh member within a patient substantially adjacent the sternum and removing the mesh member after ultrasound has been applied and the approximated portions of the sternum have substantially healed.

* * * * *